US00PP13599P3

(12) United States Plant Patent
Boeder

(10) Patent No.: US PP13,599 P3
(45) Date of Patent: Feb. 25, 2003

(54) CHRYSANTHEMUM PLANT NAMED 'FIJI SUNNY IMPROVED'

(75) Inventor: Mark Roland Boeder, West Wittering (GB)

(73) Assignee: Cleangro Limited (GB)

( * ) Notice: Subject to any disclaimer, the term of this patent is extended or adjusted under 35 U.S.C. 154(b) by 81 days.

(21) Appl. No.: 09/851,652

(22) Filed: May 8, 2001

(65) Prior Publication Data

US 2002/0170101 P1 Nov. 14, 2002

(51) Int. Cl.[7] ..... A01H 5/00
(52) U.S. Cl. ..... Plt./289
(58) Field of Search ..... Plt./289, 288, 295

(56) References Cited

U.S. PATENT DOCUMENTS

PP10,066 P 10/1997 Wain ..... Plt./288
PP10,236 P 2/1998 Wain ..... Plt./289

*Primary Examiner*—Bruce R. Campell
*Assistant Examiner*—Michelle Kizilkaya
(74) *Attorney, Agent, or Firm*—Howray Simon Arnold & White, LLP

(57) ABSTRACT

A new variety of Chrysanthemum plant named 'Fiji Sunny Improved,' characterized by its flat capitulum form; early flowering; decorative type inflorescences, strong and long peduncles; numerous ray florets per inflorescence; numerous inflorescences per plant when grown as a spray; and bright yellow ray florets.

1 Drawing Sheet

LATIN NAME OF THE GENUS AND SPECIES

Botanical classification: *Dendranthema grandiflora.*

VARIETY DENOMINATION

The new Chrysanthemum variety denomination is 'Fiji Sunny Improved.'

BACKGROUND OF THE INVENTION

The present invention comprises a new and distinct cultivar of Chrysanthemum botanically known as *Dendranthema grandiflora*, and referred to by the cultivar name 'Fiji Sunny Improved.'

'Fiji Sunny Improved', identified as CGC 97012, originated from a spontaneous whole plant mutation, found by Mark Boeder in a controlled testing program at Chichester, West Sussex, United Kingdom of the variety 'White Fiji' (U.S. Plant Pat. No. 10,066). The new variety 'Fiji Sunny Improved' has been asexually reproduced by vegetative cuttings at Chichester, West Sussex, United Kingdom and the distinguishing characteristics are retained through successive generations of asexual reproduction.

BRIEF SUMMARY OF THE INVENTION

'Fiji Sunny Improved' is a cut type of Chrysanthemum plant variety having a flat capitulum form, decorative type inflorescences and bright yellow ray florets.

Comparison with Parent

Plants of the new Chrysanthemum variety 'Fiji Sunny Improved' are similar to the cultivar 'White Fiji' in plant habitat and growth rate. In side-by-side comparisions at Chichester, West Sussex, United Kingdom, under commercial practice, plants of the new Chrysanthemum variety 'Fiji Sunny Improved' differed from plants of the parent cultivar 'White Fiji' in the following characteristics.

1. The new variety 'Fiji Sunny Improved' produces yellow flowers whereas the original cultivar 'White Fiji' produces white flowers

Comparision with Other Varieties

Plants of the new Chrysanthemum variety 'Fiji Sunny Improved.' are similar to the cultivar 'Bright Yellow Fiji' (U.S. Plant Pat. No. 10,236) in flower type, growing rate and reaction time. However, in side-by-side comparisons at Chichester, West Sussex, United Kingdom, under commercial practice, plants of the new Chrysanthemum variety 'Fiji Sunny Improved' differed from plants of the cultivar 'Bright Yellow Fiji' in the following characteristics.

1. The new variety 'Fiji Sunny Improved' produces yellow flowers whereas the cultivar 'Bright Yellow Fiji' produces slightly paler colored yellow flowers.

2. Plants of the new variety 'Fiji Sunny Improved' have a shorter inflorescence than plants of the cultivar 'Bright Yellow Fiji'.

BRIEF DESCRIPTION OF ILLUSTRATIONS

Typical specimens of the plant and flowers for the new Chrysanthemum variety 'Fiji Sunny Improved' are shown in the accompanying photogaraph. The colors shown are as true as possible within the usual limits of this kind of illustration.

FIG. 1 comprises a side perspective view of a typical flowering stem of the new variety 'Fiji Sunny Improved' grown as a cut flower.

DETAILED BOTANICAL DESCRIPTION

The following description of the new Chrysanthemum variety 'Fiji Sunny Improved' is of plants grown in a glass covered greenhouse at Chichester, West Sussex, United Kingdom in the month of December. The cultivar has not been observed under all possible environmental conditions. The phenotype may vary significantly with variations in the environment such as temperature, length of day and light intensity, without any variance in genotype. The commercial classification of the new variety is a cut Chrysanthemum.

Plants of the new variety have been grown successfully under temperature conditions averaging about 18° C. at night and about 18° C. to 24° C. during the day under light conditions of about 3,000 (cloudy conditions) to 6,000 (sunny conditions) foot candles. The plants respond well to the use of growth retardant, such as one B9 treatment at about 2 gram/liter. To produce a commercial product the plants may be pinched once or may be grown without a pinch. It has been observed that the shelf life of the new variety is about 21 days with a response time of about 7.5 weeks.

The new variety may be produced as a spray (center bud removed) or disbud (lateral buds removed). The following description is with respect to a plant produced as a cut flower without pinching. In the description of this new Chrysanthemum variety, color values have been taken from The Royal Horticultural Society Colour Chart (R.H.S.C.C.).

Plant

Plant type: Decorative type cut chrysanthemum.
Habit: Upright.
Height: 75–100 cm.
Response time: 7.5 weeks.
Vigor: Moderate.
Shelf Life: Near 21 days.
Disease (susceptibility or resistance observed): No observations.
Growth retardant type and treatment: 1 application B9 after 3 weeks in short days (13 hours of darkness) of 2 gram/liter.
Propagation:
*Type.*—Terminal tip cuttings.
*Time to rooting.*—14 days with soil temperatures of 22° C.
*Rooting habit.*—Uniform, fine, fibrous and well branched.

Foliage

Compound or single: Single.
Arrangement of Leaves: Alternate.
Shape of leaf: Typical 5 lobed.
Size of leaf:
*Width (cm).*—5.0–6.0.
*Length (cm).*—8.0–9.5.
Leaf apex: Mucronate.
Base: Cordate.
Margin: Palmately lobed.
Surface characteristics:
*Top.*—Slightly pubescent.
*Bottom.*—Slightly pubescent.
Petiole:
*Color.*—147A.
*Length.*—1.5–2.0 cm.
Venation (describe): Prominent on under surface. Color: Upper side: 147B. Under side: 147B.
Color:
*Mature leaf.*—Upper side: 147A; Under side: 147B.
*Young leaf.*—Upper side: 147A; Under side: 147B.

Flower

Flower type: Decorative.
Number of blossoms per branch: 8–14.
Inflorescence form: Cyme.
Depth of fully expanded blossoms: 1.2–2.0 cm.
Diameter of fully expanded blossoms: 1.3–2.0 cm.
Anemone center diameter: N/A.
Phyllaries:
*Number.*—15–25.
*Color.*—Near 137A.
*Length.*—0.6–1.1 cm.
*Width.*—0.4–0.6 cm.
Peduncle: Peduncle length is shortest at the terminal flower and progressively longer moving down the stem; longest length is on average 14–17(cm), shortest length is on average 11–13 (cm).
*Length.*—11–17 cm.
*Color.*—137B.
*Surface.*—Pubescent.
*Texture.*—Glabrous.
Ray florets:
*Form/shape.*—Elongated.
*Texture/appearance.*—Satiny, smooth.
*Number per flower.*—250–300.
*Length.*—3.0–4.0 cm.
*Width.*—1.1–1.6 cm.
*Apex.*—Denate.
*Base.*—Acute.
*Margin.*—Entire.
Disc florets:
*Form/shape.*—Tubular.
*Number per flower.*—5–15.
*Length.*—About 2 mm.
*Width.*—About 1 mm.
*Diameter of disc.*—<0.5 cm.
Fragrance: Moderate.
Flower Bud (at onset of color):
*Length.*—0.8–1.0 cm.
*Diameter.*—1.0–1.5 cm.
*Form/shape.*—Spherical.
General flower color:
*1. Ray florets, upper side.*—Immature: 6A. Mature: 6A. Older/Fading: 6B.
*2. Ray florets, under side.*—Immature: 8A. Mature: 8A. Older/Fading: 8B.
*3. Disc florets.*—Immature: 154A. Mature: 12B.
Flower progression with age: Color fades slightly when flowers age.

Reproductive Organs

Androecium: Present on disc florets only.
*Anther shape.*—Thread.
*Anther color.*—12A.
*Pollen quantity.*—Moderate.
Gynoecium: Present on both ray and disc florets.
*Style color.*—151B.
*Style length.*—About 0.1 cm.
Seed production: Has not been observed.

What is claimed is:

1. A new and distinct variety of Chrysanthemum plant, substantially as described and illustrated herein.

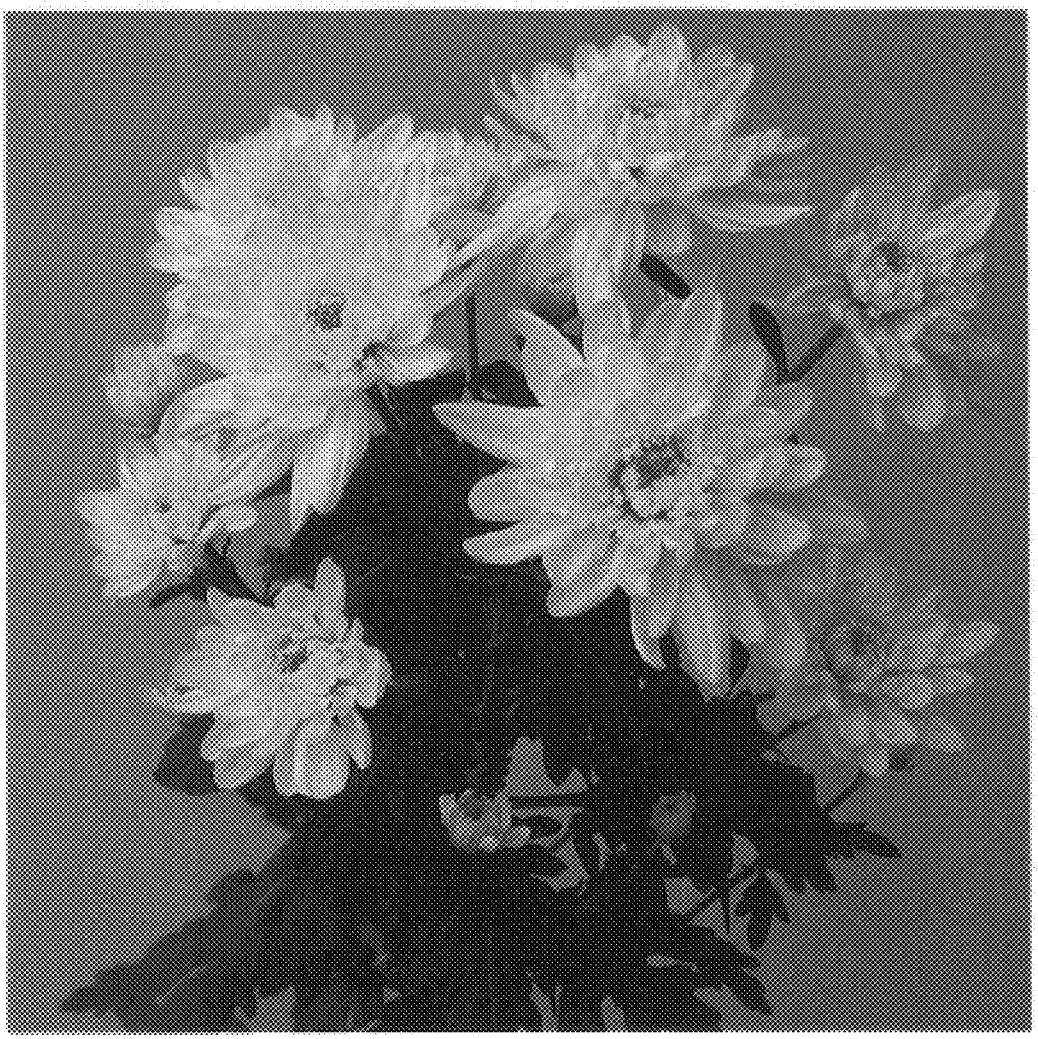

* * * * *